(12) United States Patent
van Drongelen

(10) Patent No.: US 6,560,479 B2
(45) Date of Patent: May 6, 2003

(54) ELECTRODE DISCONNECT SYSTEM AND METHOD FOR MEDICAL SIGNAL MONITORING SYSTEM

(75) Inventor: Wim van Drongelen, Madison, WI (US)

(73) Assignee: Viasys Healthcare Inc., Madison, WI (US)

( * ) Notice: Subject to any disclaimer, the term of this patent is extended or adjusted under 35 U.S.C. 154(b) by 134 days.

(21) Appl. No.: 09/761,955

(22) Filed: Jan. 17, 2001

(65) Prior Publication Data

US 2002/0095097 A1 Jul. 18, 2002

(51) Int. Cl.$^7$ ................................................ A61B 5/04
(52) U.S. Cl. ...................................................... 600/544
(58) Field of Search ................................ 600/300, 309, 600/322, 345, 437, 481, 485, 490, 500, 503–504, 508–509, 526–529, 549, 561, 587, 554, 555, 558, 559; 128/920–924, 897, 898; 341/83–85, 87

(56) References Cited

U.S. PATENT DOCUMENTS

| | | | | |
|---|---|---|---|---|
| 3,696,808 A | * | 10/1972 | Roy et al. | 324/76.33 |
| 5,279,305 A | * | 1/1994 | Zimmerman et al. | 128/903 |
| 5,287,859 A | * | 2/1994 | John | 600/544 |
| 5,724,025 A | | 3/1998 | Tavori | |
| 5,724,032 A | | 3/1998 | Klein et al. | |
| 5,951,484 A | * | 9/1999 | Hoium et al. | 600/515 |
| 6,050,940 A | | 4/2000 | Braun et al. | |
| 6,224,549 B1 | * | 5/2001 | Drongelen | 600/300 |

OTHER PUBLICATIONS

Nicolet Biomedical, "Bravo EEG Acquisition User Guide," Jun. 1998, Madison, Wisconsin.
Nicolet Biomedical, "Bravo Electromiography and Nerve Conduction Studies Reference Guide," Dec. 1998, Madison, Wisconsin.
Nicolet Biomedical, "Bravo EP Evoked Potential Guide," Jun. 1998, Madison, Wisconsin.
Wim Van Drongelen, U.S. patent application 09/295,167, "Medical Signal Monitoring and Display," filed Apr. 20, 1999.
William J. Lutz, U.S. patent application 09/320,613, "Time Frame Synchronization of Medical Monitoring Signals," filed May 26, 1999.

* cited by examiner

Primary Examiner—Samuel G. Gilbert
(74) Attorney, Agent, or Firm—Foley & Lardner

(57) ABSTRACT

A system and method for easily and rapidly disconnecting electrode signals from and connecting electrode signals to amplifiers in, e.g., a medical signal monitoring system. A switching device is provided between an electrode and a corresponding electrophysiologic signal amplifier forming a signal channel. A channel disconnect selection user interface is provided for indicating selected channels. A channel disconnect user interface is provided, whereby an operator may indicate in a single action that electrode signals in the channels selected using the channel disconnect selection user interface are to be disconnected from, and reconnected to, their respective amplifiers. Electrode signals in the selected channels may be disconnected from and reconnected to their respective amplifiers automatically in timed relation to electrical stimulation provided to a subject.

31 Claims, 4 Drawing Sheets

FIG. 2

| Chan. | Mode | - Input | + Input | Label | Amplifier Gain | Low Freq. | High Freq. | Slope Low | Notch |
|---|---|---|---|---|---|---|---|---|---|
| 1 | Refer... | 01 | REF | 01 | 500 | 0.2 | 500 | 12 | On |
| 2 | Refer... | 02 | REF | 02 | 500 | 0.2 | 500 | 12 | On |
| 3 | Refer... | 03 | REF | 03 | 500 | 0.2 | 500 | 12 | On |
| 4 | Refer... | 04 | REF | 04 | 500 | 0.2 | 500 | 12 | On |
| 5 | Differe... | 10 | 11 | 10-11 | 500 | 0.2 | 5000 | 12 | On |
| 6 | Differe... | 12 | 13 | 12-13 | 500 | 0.2 | 5000 | 12 | On |
| 7 | Differe... | 14 | 16 | 14-15 | 500 | 0.2 | 5000 | 12 | On |
| 8 | Differe... | 16 | 17 | 16-17 | 500 | 0.2 | 5000 | 12 | On |

ELECTRODE DISCONNECT SYSTEM AND METHOD FOR MEDICAL SIGNAL MONITORING SYSTEM

FIELD OF THE INVENTION

The present invention pertains generally to medical monitoring methods and devices for analyzing and displaying electrophysiologic signals, and more particularly to systems and methods for connecting and disconnecting electrophysiologic signals detected at electrodes placed on a subject to and from detection amplifiers employed in such a medical monitoring device.

BACKGROUND OF THE INVENTION

Medical monitoring involves monitoring the body of a subject to determine the state of health of the subject and to detect, identify, and diagnosis changes or abnormalities in the state of the body which may be indicative of problems, or for treatment evaluation. Medical monitoring may involve, for example, the motion of a subject's body, temperature or chemical changes of the subject's body, and/or audible or electrical signals reflected or generated by the subject's body. For example, electroencephalography (EEG) is a form of medical monitoring wherein the electrical potentials of the subject's brain are monitored by attaching electrodes to the subject's scalp. In electromyography (EMG), electrical activity generated in the subject's muscles is monitored using surface and/or needle recording electrodes. Medical monitoring may take place when a subject is at rest, in motion, or during the performance of a medical procedure. In some cases, medical monitoring involves monitoring the response of a subject to a stimulus. For example, evoked potential (EP) monitoring may be used to detect the electrical response of a subject's nervous system to audible, visual, or electrical stimuli. Medical monitoring involving stimulus and response detection may be used in combination with EMG and various other medical monitoring methods as well.

Monitoring of the various physiologic signals generated by a subject's body is typically performed using dedicated devices and/or systems. For example, EEG monitoring may be performed using a dedicated EEG monitoring system, by attaching electrodes to a subject to detect the electrical potential of the subject's brain, amplifying and filtering the signals received from the electrodes for the desired frequency range of interest for EEG analysis, and providing the amplified and filtered signals to an EEG analysis system including software for further manipulating the EEG signals for analysis and display on an EEG system monitor. Similarly, EMG monitoring may be performed using a dedicated EMG monitoring system, by placing electrodes on the subject to detect electrical activity generated in the subject's muscles, amplifying and filtering the signals detected by the electrodes for the desired frequency range of interest for EMG signals, and providing the amplified and filtered signals to an EMG analysis system including software for further manipulating the EMG signals for analysis and display on an EMG system monitor. Other signals of interest, e.g., vital signs, may be monitored in a similar manner, with a separate dedicated system provided for each type or modality of monitored signal of interest. Each such dedicated monitoring system may include or be connected to a system for providing stimulus to a subject, and for analyzing the particular detected signal of interest in response to the stimulus provided.

U.S. patent application Ser. No. 09/295,167, entitled "Medical Signal Monitoring and Display", by Wim Van Drongelen, and assigned to the assignee of the present application, describes a medical signal monitoring system and method providing the capability for an operator of the system to display and analyze physiologic signals of various types, frequencies, and modalities. Such a system may be provided with data from various physiologic signal acquisition systems, including systems for acquiring electrophysiologic signals from electrodes positioned on the subject. The system may further be connected to auditory, visual, and/or electrical stimulator systems, for controlling the providing of stimulation to a subject, while analyzing the physiologic signals received in response to the stimulus provided. Such a system includes an operator-friendly user interface which allows an operator of the system to designate and control, display, and analyze the physiologic signals received by the system and stimulus provided thereby. Such an integrated system provides a full range of diagnostic capability in a single device for use in a doctor's office, operating room, intensive care unit, or emergency department.

In a typical application of a medical signal monitoring system, a plurality of electrodes may be attached to the body of a subject. Electrophysiologic signals, picked up by the electrodes, are carried by leads to a signal amplifier which may be part of or separate from the medical monitoring system. Typically, the signal provided on each such lead is amplified by a separate amplifier. The amplified signals may, for example, be filtered, digitized, and provided to the medical monitoring system for analysis and display. In this manner, several electrophysiologic signals, e.g., EEG and EMG signals, produced by a subject may be monitored continuously or periodically.

At times, it may be desirable to determine a subject's response to an electrical signal applied to the subject (e.g., transcranial electric stimulation). A strong (high voltage) electrical signal applied to a subject's body will be picked up by electrodes placed on the subject for detecting electrophysiologic signals. The stimulation signal will typically be much larger than any electrophysiologic signal produced by the subject's body, especially in the area near where the electrical stimulation is provided. Thus, the electrical stimulation will tend to saturate the amplifiers which are connected by leads to electrodes placed on the subject near the point of electrical stimulation. Such over-saturation prevents recording of the response to the stimulation and may damage the amplifiers. Thus, to protect the amplifiers from damage, electrodes attached to a subject's body near the point of electrical stimulation (and which are not used for monitoring the subject's response to the stimulation) are typically physically removed from the subject before the electrical stimulation is provided to the subject. This situation is typical for a multi-modality monitoring device. By disconnecting selected electrodes from a subject, responses occurring at other electrodes can be recorded and potential damage to the amplifier is prevented. After the electrical stimulation is provided, these electrodes must be reattached to the subject if monitoring of the desired electrophysiologic signals is to continue. Thus, in a situation where it is desired to continually monitor certain physiologic signals, while periodically performing tests involving the application of electrical signals to a subject, it may be necessary to repeatedly physically remove electrodes from a subject (or remove the amplifier inputs), before electrical stimulation, and reattach the electrodes to the subject (or reattach the amplifier inputs), after stimulation is completed. This process is obviously time-consuming, and prone to error, as each time an electrode is removed from a subject there is the possibility that the electrode will not be placed back in the proper position on the subject (or reattached to the correct amplifier input).

What is desired, therefore, is a system and method for easily and quickly disconnecting electrophysiologic signals provided from electrodes attached to a subject from the amplifiers to which such signals are provided, when desired, such as before applying an electrical stimulation signal to the subject, and for easily and quickly reconnecting the electrophysiologic signals to the amplifiers after electrical stimulation is complete. Preferably, such a system and method provides for disconnecting electrophysiologic signals from the amplifiers without physically removing the electrodes from a subject or physically removing electrode leads from an amplifier input.

SUMMARY OF THE INVENTION

The present invention provides a system and method for easily and rapidly disconnecting medical signal monitoring electrodes from and connecting such electrodes to amplifiers in a medical signal monitoring system. In accordance with the present invention, electrodes positioned on a subject to detect electrophysiologic signals produced thereby are connected via leads and switching devices to signal amplifiers. Each such electrode, lead, switching device, and amplifier combination forms a signal channel. The switching devices are controlled by switching device control signals provided by a system processor. The system processor provides a channel disconnect selection graphical user interface to an operator on an operator display, whereby the operator may indicate selected ones of the signal channels. A channel disconnect user interface is also provided, whereby an operator may indicate in a single action that signals from the electrodes in the channels selected using the channel disconnect selection user interface are to be disconnected from their respective amplifiers. Similarly, signals from the electrodes in the selected channels may be reapplied to their respective amplifiers in a single action using the channel disconnect user interface. When the channel disconnect user interface is selected, the switching devices in the channels selected using the channel disconnect selection user interface are opened, to disconnect the signals provided by the electrodes from the corresponding amplifiers. When the channel disconnect user interface is deselected, the switching devices in the channels selected using the channel disconnect selection user interface are closed, thereby reconnecting the signals provided from the electrodes to the corresponding amplifiers in the selected channels. In channels which are not selected using the channel disconnect selection user interface, the switching devices remain closed when the channel disconnect user interface is selected, such that signals from the electrodes are provided to the corresponding amplifiers in those channels regardless of whether the channel disconnect user interface is selected or not.

An electrode disconnect system in accordance with the present invention may be used to easily disconnect electrode signals from their corresponding amplifiers in a medical signal monitoring system, e.g., before an electrical stimulus is applied to the subject, without requiring physical removal of electrodes from a subject or the physical removal (unplugging) of electrode leads from an amplifier circuit. As discussed above, high voltage electrical stimulus signals applied to a subject may saturate amplifiers connected to electrodes placed on the subject near the point where the stimulation is applied. Before applying such electrical stimulation, the channel disconnect selection user interface may be used to indicate selected channels in which the electrodes should be disconnected from their corresponding amplifiers when the electrical stimulation is provided to the subject. Just before electrical stimulation is provided, the channel disconnect user interface is selected, thereby disconnecting the electrodes selected using the channel disconnect selection user interface from their corresponding amplifiers. For example, in response to selecting the channel disconnect user interface, switching devices connected between the electrodes selected using the channel disconnect selection user interface and inputs to corresponding amplifiers are opened, e.g., via control signals provided to the switching devices by the system processor. At this point, electrical stimulation can be provided to the subject without risk of saturating the amplifiers in the selected signal channels, and without physically removing any electrodes from the subject or electrode leads from an amplifier circuit. After electrical stimulation is complete, the channel disconnect user interface may be simply deselected. In response to deselecting the channel disconnect user interface, the electrodes in the channels selected using the channel disconnect selection user interface are reconnected to the inputs of their corresponding amplifiers by, e.g., closing the switching devices in the selected channels. Thus, an electrode disconnect system and method in accordance with the present invention may be used in combination with a medical signal monitoring system for monitoring various electrophysiologic signals from a subject, to facilitate periodically performing tests requiring the application of electrical stimulation to the subject using such a system, without requiring physically disconnecting electrodes from a subject (or from an amplifier's input connection box) prior to such testing, to prevent amplifier saturation, and then physically reconnecting the electrodes to a subject (or to the amplifier's input connection box) after a stimulation test is complete.

In accordance with the present invention, the electrodes in signal channels selected using the channel disconnect selection user interface may be disconnected from and reconnected to their corresponding signal amplifiers, e.g., by opening and closing the switching devices in such channels, either directly in response to the selection and deselection, respectively, of the channel disconnect user interface, or automatically in timed relation to an applied electrical stimulus signal. In the latter case, the channel disconnect user interface, or another user interface, may be used to enable the automatic disconnection and reconnection of the electrodes from their corresponding amplifiers in selected signal channels when an electrical stimulus signal is applied to a subject. When automatic connection and disconnection is enabled, the electrodes in signal channels selected using the channel disconnect selection user interface will be automatically disconnected from their corresponding amplifiers just prior to the application of an electrical stimulus signal to a subject, and automatically reconnected to their corresponding amplifiers following a delay time after delivery of the stimulus signal is complete. Delivery of the electrical stimulus signal and control of switching devices in the selected signal channels to provide such automatic electrode signal disconnection and reconnection may be controlled by the medical monitoring system processor. The time periods between automatic electrode disconnection and the beginning of electrical stimulation and between the end of electrical stimulation and automatic electrode reconnection may be user selectable.

Further objects, features, and advantages of the present invention will be apparent from the following detailed description taken in conjunction with the accompanying drawings.

BRIEF DESCRIPTION OF THE DRAWINGS

In the drawings:

FIG. 2 is a screen display showing an exemplary channel disconnect selection user interface and channel disconnect user interface whereby an operator may select signal monitoring channels in a medical signal monitoring system and selectively disconnect electrode signals from and reconnect electrode signals to corresponding signal amplifiers in the selected channels with a single action using the channel disconnect user interface.

DETAILED DESCRIPTION OF THE INVENTION

Figure 1:
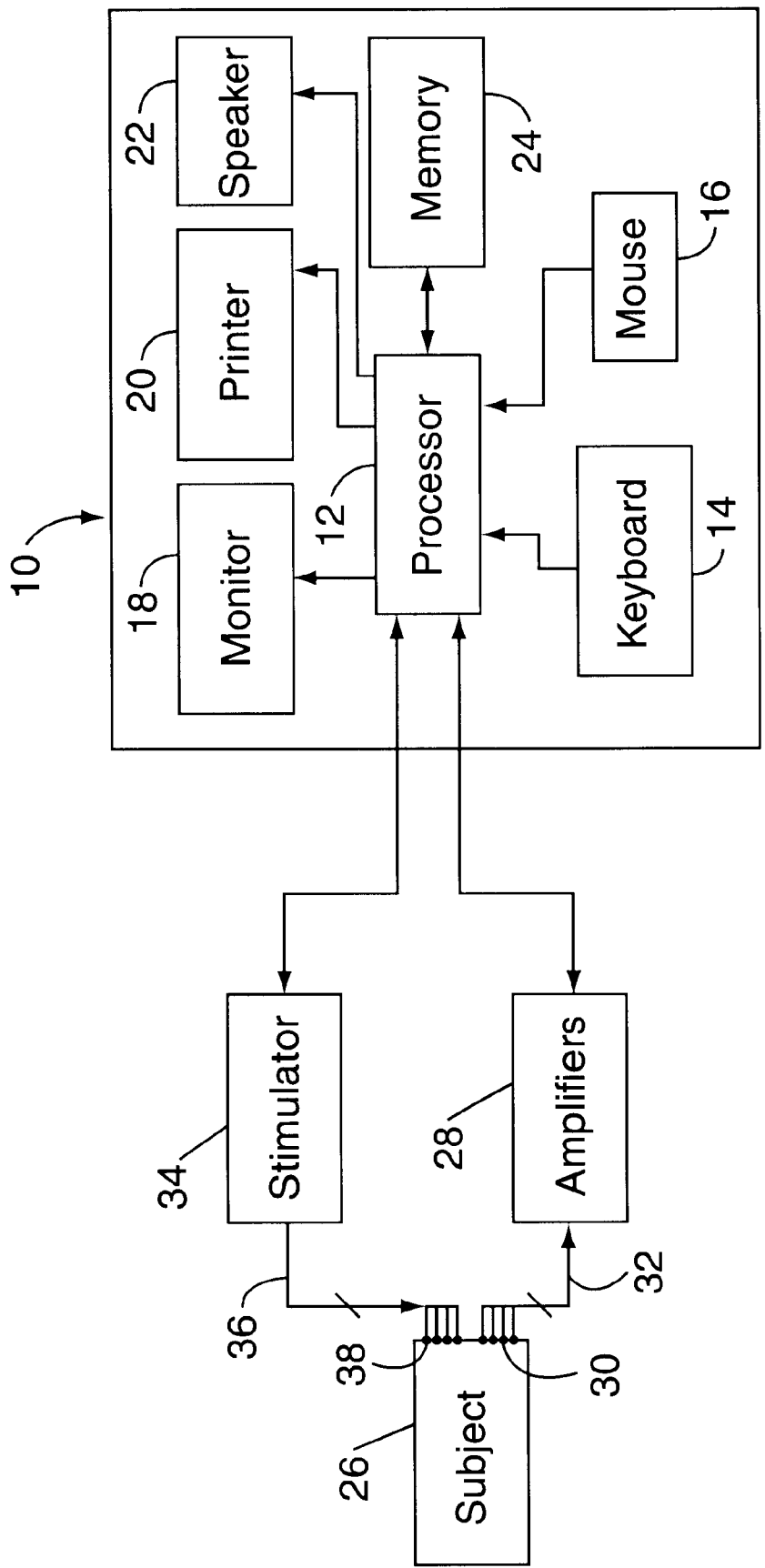
FIG. 1 is a schematic block diagram of an exemplary medical signal monitoring system employing an electrode disconnect system and method in accordance with the present invention.

The present invention provides a system and method for easily and rapidly disconnecting electrode signals from and connecting electrode signals to corresponding amplifiers in selected signal monitoring channels of a system for, e.g., monitoring medical signals, such as electrophysiologic signals detected by electrodes placed on a subject. The present invention will be described herein with reference to the exemplary incorporation thereof into an integrated medical signal monitoring system which may be used for monitoring and analyzing a variety of electrophysiologic signals, as well as for providing electrical and other stimulus to a subject and detecting and analyzing the subject's response thereto. Such an integrated medical signal monitoring system is described, for example, in U.S. patent application Ser. No. 09/295,167, entitled "Medical Signal Monitoring and Display," filed on Apr. 20, 1999, by Wim Van Drongelen, and assigned to the assignee of the present application, the disclosure of which is incorporated herein by reference. It should be understood, however, that the present invention may also be incorporated in, and used in combination with, other and/or more basic medical signal monitoring systems which are only designed to monitor a single type or modality of electrophysiologic signal. More generally, the present invention may be employed in any system where it is desirable to rapidly and easily disconnect collected source signals being monitored from, and reconnect such source signals to, corresponding signal amplifiers.

A basic hardware configuration for a medical signal monitoring system 10 incorporating and employing an electrode disconnect system and method in accordance with the present invention is illustrated in, and will be described with reference to, FIG. 1. A medical signal monitoring system 10 may be implemented using a conventional computer system having conventional computer peripheral devices. For example, monitoring system 10 may be implemented on a conventional personal computer processor 12. Due to the large number of computations performed by the processor 12, a computer employing a fast processor, such as a Pentium 800 MHz Processor, or faster, is preferred. It should be understood that the present invention may be implemented using other types of general purpose or special purpose programmable computers or processors 12.

The processor 12 is preferably provided with conventional computer peripherals. For example, the processor 12 preferably includes conventional input devices such as, for example, a keyboard 14 and mouse 16. Other types of input devices, such as a microphone for voice recognition control of the system, may be employed. Conventional output devices which may be employed with the processor 12 include a computer monitor 18, printer 20, and speaker 22 for providing audio output from the processor 12. The processor 12 preferably is also provided with conventional computer memory 24, including a large disk storage capability.

The monitoring system 10 receives physiologic signals from a subject 26 via one or more signal amplifier circuits 28. (Note that the amplifier circuits 28 may be separate from or included as part of the medical signal monitoring system 10.) The amplifier circuit 28 may be connected to the subject 26 by, for example, electrodes 30 placed on the subject 26. The electrodes 30, which may be conventional electrodes as are well-known in the art, pick up electrophysiologic signals of the subject 26 and provide the signals, via leads 32, to the amplifier circuit 28. The amplifier circuit 28 amplifies the signals received from the electrodes 30, may provide some preliminary filtering of the signals, and then provides the amplified and preliminary filtered signals to the monitoring system 10 for analysis and display. In a dedicated EEG, EP, or EMG system, the amplifier circuit 28 may filter the electrode signals to a relatively narrow band of interest. However, for an integrated system, as described in the above-referenced U.S. patent application Ser. No. 09/295,167, wherein electrophysiologic signals across a broad frequency range are displayed and analyzed, a broad band of frequencies should be passed by the amplifier circuit 28 to the monitoring system 10 (e.g., at least broad enough to include the EEG and EMG bands). The signals provided to the monitoring system 10 from the amplifier circuit 28 are, therefore, preferably essentially raw signals.

The medical signal monitoring system 10 may also control the providing of stimulation signals to the subject 26 via one or more stimulator systems 34. Various different types of stimulator systems 34 may be employed, including stimulator systems for providing electrical, auditory, or visual stimulation. The stimulator systems 34 may be connected to the subject 26 via, for example, conventional leads 36 and electrodes 38 positioned on the subject 46 for providing electrical stimulation to the subject 46. The stimulator system 34 preferably provides a signal back to the monitoring system 10 indicating the time at which a stimulation signal is provided to the subject 46. This signal allows the monitoring system 10 to synchronize the stimulation signals provided to the subject 46 with response signals received from the amplifier circuit 28 for proper analysis and display of the relationship between the stimulus and response signals.

It should be understood that each of the hardware components illustrated in FIG. 1 may be implemented in a conventional manner, using conventional commercially available hardware. Also, the various hardware systems illustrated in FIG. 1 may be connected together in a conventional manner, using conventional leads, cabling, connectors, etc. Alternatively, the various hardware systems illustrated in FIG. 1 may be connected together via a network bus topology, such as, for example, an IEEE 1394 high-speed serial bus topology. In the latter case, the stimulus signals provided by the stimulator device 34 and the response signals detected by the amplifier circuit 28 may be timeframe synchronized in the manner described in co-pending U.S. patent application Ser. No. 09/320,613, entitled "Time Frame Synchronization of Medical Monitoring Signals," filed on May 26, 1999, by William J. Lutz, and assigned to the assignee of the present application.

Figure 4:
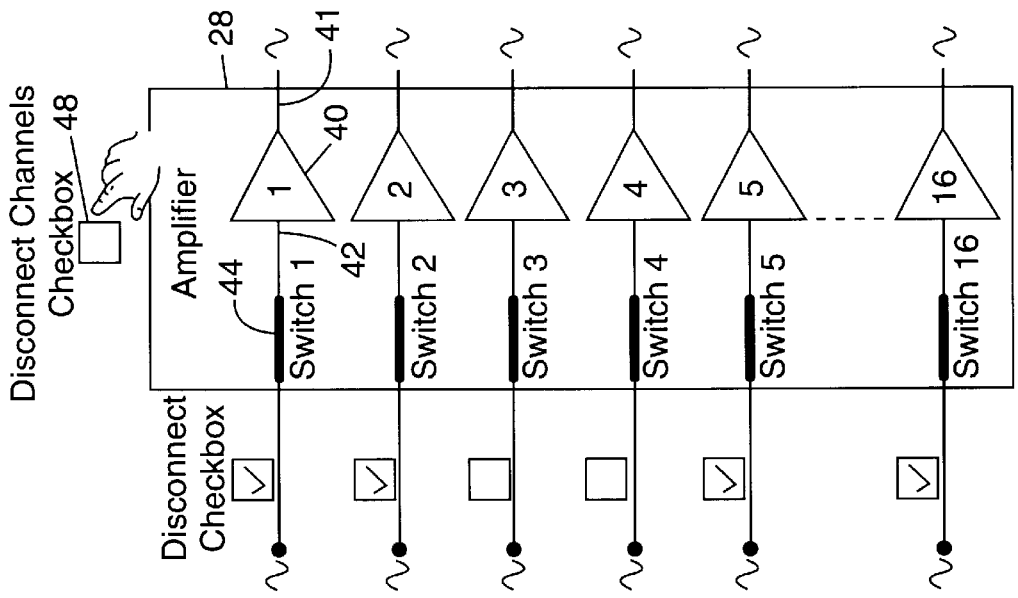
FIG. 4 is a schematic illustration of an exemplary medical signal monitoring system amplifier circuit showing all of the switching devices connected between electrodes and corresponding amplifiers in all signal channels closed, to connect signals provided on the electrodes to corresponding amplifiers, when the channel disconnect user interface is deselected by an operator.
Figure 3:
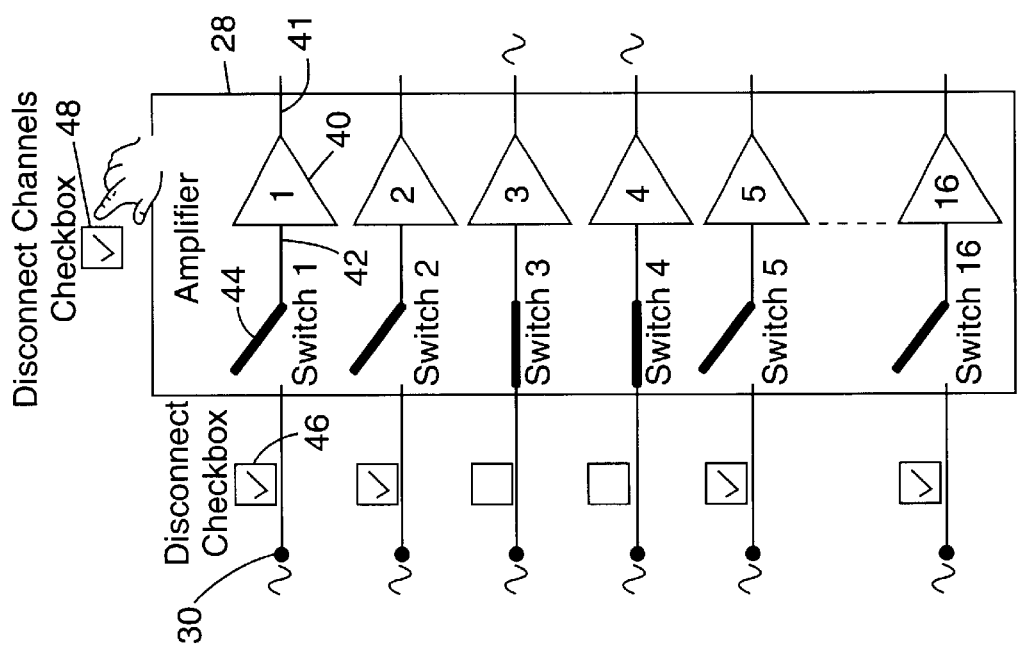
FIG. 3 is a schematic illustration of an exemplary medical signal monitoring system amplifier circuit showing open switching devices connected between electrodes and corresponding amplifiers in selected signal channels when a channel disconnect user interface is selected by an operator.

Exemplary amplifier circuits 28 in accordance with the present invention are illustrated, in schematic fashion, in FIGS. 3 and 4. An amplifier circuit 28 in accordance with the present invention includes a plurality of signal amplifiers 40. The signal amplifiers 40 may be implemented in a conventional manner using conventional discreet or integrated analog amplifier circuit technology. As discussed above, the output sides 41 of the amplifiers 40 are connected in a conventional manner to a medical monitoring system 10 to provide, e.g., amplified electrophysiologic signals to the system processor 12 for analysis and display. In accordance with the present invention, the input side 42 of each amplifier 40 in the amplifier circuit 28 is connected to a switching device 44. The switching devices 44 can be implemented as solid state switching devices, such as using one or more transistors, or as relays which are responsive to switching device control signals provided from the medical monitoring system processor 12 to open and close the switching devices 44. The switching devices 44 are connected to the input sides 42 of their corresponding amplifiers 40 such that a switching device 44 is positioned between each electrode 30, which may be attached to a subject 26 for detecting electrophysiologic signals therefrom, and the corresponding amplifier 40 for amplifying the electrophysiologic signals thus detected. Thus, an amplifier 40 with its corresponding switching device 44 forms a signal channel for providing an electrophysiologic signal provided from an electrode 30, attached to a subject 26, to the medical signal monitoring system 10. When a switching device 44 is closed, the electrophysiologic signal from the corresponding electrode 30 is provided to the corresponding amplifier 40, which amplifies the signal before providing the signal to the medical signal monitoring system 10 for analysis and display. When a switching device 44 is opened, however, an electrophysiologic signal picked up by electrode 30 is prevented from being applied to the input side 42 of the corresponding amplifier 40.

The signal amplifiers 40 employed in medical signal monitoring applications are designed to amplify relatively low-level electrophysiologic signals detected by electrodes 30 placed on or in a subject 26. A large (i.e., high voltage) electrical signal, such as from an electrical stimulus signal provided to a subject 26, which is picked up by an electrode 30 may, therefore, cause saturation of and, possibly, damage to such an amplifier 40 connected thereto. By providing a controllable switching device 44 between each electrode 30 and its corresponding amplifier 40, in accordance with the present invention, the switching device 44 may be manually or automatically controlled to open before such an electrical stimulus signal is applied to the subject 26, thereby preventing saturation of, and potential damage to, the corresponding amplifier 40. The switching devices 44 thus allow for an amplifier 40 in the amplifier circuit 28 to be protected from large electrical signals, such as those resulting from electrical stimulation of the subject 26, without having to physically remove the corresponding electrode 30 from the subject 26 or physically unplug electrode leads from an amplifier connector box. The switching devices 44 also allow for the amplifiers 40 to be easily reconnected to their corresponding electrodes, e.g., after electrical stimulation is complete.

An electrode disconnect system and method in accordance with the present invention preferably includes an easy to use graphical user interface which allows an operator to identify selected channels in a multiple channel medical monitoring system for which signals detected by electrodes in such channels are selectively disconnected from and reconnected to corresponding amplifiers in such channels, when desired, as well as a graphical user interface for actually controlling disconnecting and reconnecting the electrode signals from and to the amplifiers in such preselected channels in a single action, or enabling automatic disconnection and reconnection thereof. The first such graphical user interface, referred to as a channel disconnect selection user interface 46, is associated with each signal monitoring channel in, e.g., a medical signal monitoring system 10. The channel disconnect selection user interface 46 may be implemented, for example, as a checkbox or other menu interface which is selected by an operator to indicate that a signal channel is enabled to have the electrode signal disconnected from the corresponding amplifier in such channel when desired, e.g., during the application of electrical stimulation to a subject on which the electrodes 30 are positioned. The second such user interface is a channel disconnect user interface 48. The channel disconnect user interface 48 may be implemented as a single checkbox or other menu interface which may be selected by an operator. When the channel disconnect user interface 48 is selected, the switching devices 44 in each channel selected using the channel disconnect selection user interface 46 may be opened, thereby disconnecting the electrode signals from their corresponding amplifiers in such channels (see FIG. 3). When the channel disconnect user interface 48 is deselected, the switching devices 44 are closed (see FIG. 4). In channels for which the channel disconnect selection user interface 46 is not selected, the state of the switching devices 44 in such channels is not affected by selection of the channel disconnect user interface 48 (e.g., switching devices 44 within such channels remain closed, see, e.g., the switching devices 44 in channels 3 and 4 of FIGS. 3 and 4). These graphical user interfaces 46 and 48 may be generated in a conventional manner by the system processor 12 of a medical monitoring system 10 in which an electrode disconnect system and method in accordance with the present invention is employed, may be displayed on the system monitor 18, and may be operated by a user input device, such as a keyboard 14 or mouse 16. Such graphical user interfaces allow an operator to select easily those channels for which electrode signals are to be disconnected from the corresponding amplifiers, e.g., during the application of electrical stimulation to a subject, and to easily disconnect such electrode signals from their corresponding amplifiers, and then reconnect the electrode signals to their corresponding amplifiers 40, without removing any electrodes 30 from a subject 26 or unplugging electrode leads, in a single action, and without affecting the operation of other signal channels which are to remain in use, e.g., during electrical stimulation provided to the subject 26.

An exemplary graphical user interface 50 which incorporates channel disconnect selection 46 and channel disconnect 48 user interfaces is illustrated in FIG. 2. The exemplary graphical user interface 50 may be employed in an integrated medical signal monitoring system, such as is described in the above-referenced U.S. patent application Ser. No. 09/295,167, to allow a user of such a system to define the signals which are to be detected in each of several signal detection channels including an electrode 30 attached to a subject 26, a switching device 44, and an amplifier 40, as described previously. Such a graphical user interface may be generated in a conventional manner by the system processor 12 of such a medical monitoring system 10, and displayed on a system display or monitor 18. An operator may interact with such a user interface 50 in a conventional manner using the system keyboard 14, mouse 16, or other user input device. The exemplary graphical user interface 50 includes a variety of menu selections 52 for each channel, which allow a user to identify, e.g., the −/+ inputs for each channel, a label for each channel, low- and high-frequency cutoff for each channel, amplifier gain, low-frequency cutoff slope, whether audio signals are to be produced from the signal detected on the defined channel, etc. The characteristics of each channel thus defined is displayed in a window 54 provided on the graphical user interface 50. The graphical user interface 50 may, therefore, be used to define new signal detection channels for an integrated medical signal monitoring system 10, or to edit previously defined channels.

Included among the menu options 52 used to define each signal channel is a channel disconnect selection user interface 46, implemented, e.g., as a checkbox. If the channel disconnect selection user interface 46 for a channel is selected, any electrode signal detected on such a channel may be disconnected from its corresponding amplifier when the channel disconnect user interface 48, which is also provided on the user interface 50, is selected, as discussed above. If the channel disconnect selection user interface 46 is not selected for any particular defined signal channel, the state of the switching device 44 provided between the electrode 30 and amplifier 40 in such channel will not be affected (e.g., will remain closed) whether or not the channel disconnect user interface 48 is selected.

Figure 5:
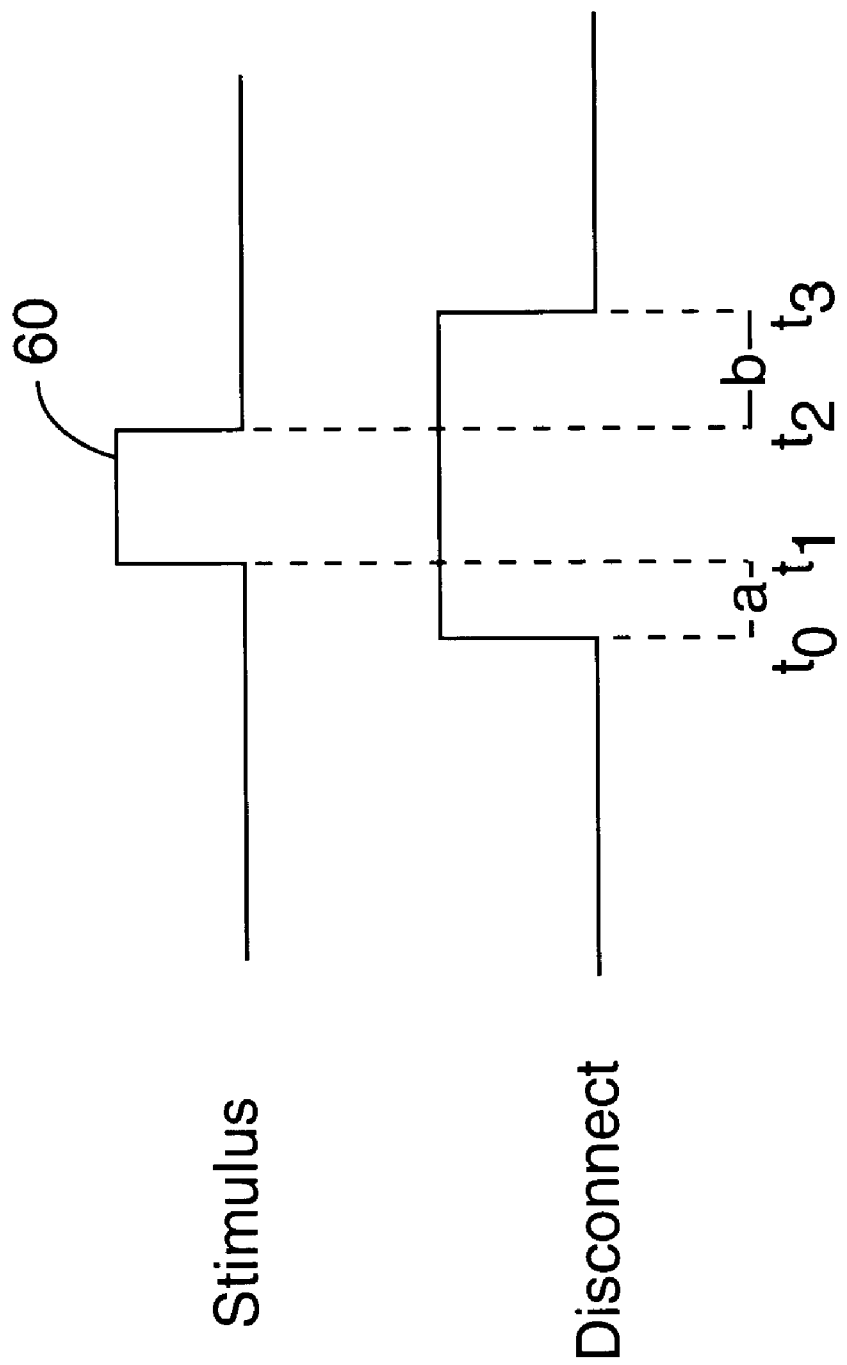
FIG. 5 is a timing diagram illustrating the timing of the automatic disconnection of electrode signals from and reconnection of electrode signals to corresponding amplifiers in selected signal channels with respect to an electrical stimulus signal provided to a subject in an electrode disconnect system and method in accordance with the invention.

The electrodes 30 in signal channels selected using the channel disconnect selection user interface 46 may be disconnected from and reconnected to their corresponding signal amplifiers 40, e.g., by opening and closing the switching devices 44 in such channels either directly in response to the selection and deselection, respectively, of the channel disconnect user interface 48, or automatically in timed relation to an electrical stimulus signal applied to a subject 26. In the latter case, the channel disconnect user interface 48, or another user interface, may be used to enable and disable the automatic disconnection and reconnection of the electrodes 30 from their corresponding amplifiers 40 in selected channels when an electrical stimulus signal is provided. When such automatic disconnection/reconnection is enabled, the electrodes 30 in signal channels selected using the channel disconnect selection user interface 46 are automatically disconnected from their corresponding amplifiers 40 just prior to the application of an electrical stimulus signal to a subject 26, and automatically reconnected to their corresponding amplifiers 40 a delay time after delivery of the stimulus signal is complete. For example, with reference to the exemplary timing diagram of FIG. 5, an electrical stimulus pulse 60 may be delivered to a subject 26 beginning at time $t_1$ and terminating at time $t_2$. In accordance with the present invention, if enabled, the electrodes 30 in signal channels selected using the channel disconnect selection user interface 46 are automatically disconnected from their corresponding amplifiers 40 at a time $t_0$, which precedes time $t_1$ by a time period a, and are automatically reconnected to the amplifiers 40 at a time $t_3$, which follows time $t_2$ by a delay time period b. The time periods a and b between automatic electrode disconnection ($t_0$) and the beginning ($t_1$) of the electrical stimulation pulse 60, and between the end ($t_2$) of electrical stimulation and automatic electrode reconnection ($t_3$) may be predetermined or user selectable using a conventional graphical user interface. Preferably, the time periods a and b are selected such that the selected electrodes 30 are disconnected from and reconnected to their corresponding amplifiers 40 before and after the application of electrical stimulation such that saturation of the amplifiers 40 is avoided and such that the electrode signals are reconnected to the amplifiers 40 in sufficient time to detect any electrophysiologic response of the subject 26 to the stimulus signal 60.

An electrode disconnect system in accordance with the present invention may be used effectively in situations where various electrophysiologic signals of a subject 26 are to be monitored continuously, with periodic monitoring of the response of selected physiological signals to electrical stimulation also required. In such an application, for example, several electrodes 30 may be positioned on a subject 26 to detect both the electrophysiologic signals which are to be monitored continually as well as those which are to be detected periodically in response to the application of electrical stimulation to the subject 26. Prior to the initiation of signal monitoring, the channel disconnect selection user interface 46 is selected for each signal channel for which the signal provided from an electrode 30 is to be disconnected from its corresponding amplifier 40, to protect the amplifier 40 from saturation and possible damage, during the application of electrical stimulation to the subject 26. Such channels may correspond, for example, to electrodes 30 positioned near the point of application of electrical stimulation to the subject 26. The monitoring and analysis of physiological signals detected at the electrodes 30 using the medical signal monitoring system 10 may then proceed, as described above. Periodically, e.g., prior to the application of electrical stimulation to the subject 26, the channel disconnect user interface 48 may be selected. In response to selection of the channel disconnect user interface 48, control signals are provided from the system processor 12 to the switching devices 44 in the signal channels which were previously selected using the channel disconnect selection user interface 46, to open the switching devices 44 therein, to disconnect the electrode signals from the amplifiers 40 in such channels. Thus, the amplifiers 40 in such channels are protected from saturation and damage, without requiring removal of any electrodes 30 from a subject 26. After completion of the providing of electrical stimulation to the subject 26, the channel disconnect user interface 48 may be deselected, in response to which the system processor 12 provides control signals to the switching devices 44 in the signal channels selected using the channel disconnect selection user interface 46, to thereby close the switching devices 44, to reconnect the electrodes 30 to the corresponding amplifiers 40 in such channels. Thus, electrode signals in selected channels may be easily and quickly connected to and disconnected from corresponding amplifiers 40 with a single action, using the channel disconnect user interface 48, and without the need for physically removing electrodes from and reattaching the electrodes to a subject 26, or unplugging electrode leads. Alternatively, the channel disconnect user interface 48, or another user interface, may be used to enable the automatic disconnection and reconnection of the selected electrodes 30 from their corresponding amplifiers 40 when the electrical stimulation is provided, as described above. Delivery of the electrical stimulus signal and control of the switching devices 44 in the selected signal channels to provide such automatic electrode disconnection and reconnection may be controlled, e.g., by the processor 12 of an integrated medical signal monitoring system 10.

It should be understood that the present invention is not limited to the particular exemplary applications and embodiments illustrated and described herein, but embraces all such modified forms thereof as come within the scope of the following claims.

What is claimed is:

1. A signal monitoring system, comprising:
   (a) a plurality of signal amplifiers;
   (b) a plurality of switching devices, wherein each one of the plurality of switching devices is connected to an input of a one of the plurality of signal amplifiers, each of the plurality of switching devices being responsive to a switching device control signal to control the switching device to prevent a signal from being applied to the input of a corresponding signal amplifier or to allow application of a signal to the input of the corresponding signal amplifier, each switching device and its corresponding signal amplifier forming a signal channel;
   (c) a channel disconnect selection user interface to allow a user to indicate selected ones of the signal channels;
   (d) a channel disconnect user interface selectable by a user; and
   (e) a processor connected to the plurality of switching devices and adapted to provide the switching device control signal to control the switching devices in each channel selected using the channel disconnect selection user interface to prevent a signal from being applied to the input of the corresponding amplifiers only in such selected channels when the channel disconnect user interface is selected and to provide the switching device control signal to control the switching devices in the selected channels to allow application of a signal to the input of the corresponding amplifiers in such selected channels when the channel disconnect user interface is deselected.

2. The signal monitoring system of claim 1 wherein the plurality of switching devices are selected from the group of switching devices consisting of transistors and relays.

3. The signal monitoring system of claim 1 comprising additionally an electrode connected by a lead to the input of each signal amplifier via a corresponding one of the switching devices.

4. The signal monitoring system of claim 1 wherein each signal amplifier is adapted to amplify an electrophysiologic signal.

5. The signal monitoring system of claim 1 wherein the channel disconnect selection user interface and the channel disconnect user interface are graphical user interfaces adapted to be displayed to a user on a display.

6. The signal monitoring system of claim 5 wherein the channel disconnect selection user interface and the channel disconnect user interface include check boxes.

7. The signal monitoring system of claim 5 wherein the channel disconnect selection user interface and the channel disconnect user interface are generated by the processor.

8. A medical signal monitoring system, comprising:
   (a) a plurality of electrodes adapted to be positioned on a subject to detect electrophysiologic signals;
   (b) a plurality of signal amplifiers coupled to the plurality of electrodes such that each electrode and a corresponding signal amplifier form a signal channel, wherein the signal amplifiers are adapted to amplify electrophysiologic signals;
   (c) a switching device connected between the electrode and the signal amplifier in each signal channel, each switching device being responsive to a switching device control signal to control the switching device to prevent a signal from being applied to a signal amplifier from a corresponding electrode, or to allow application of a signal to the signal amplifier from the corresponding electrode;
   (d) a channel disconnect selection user interface to allow a user to indicate selected ones of the signal channels;
   (e) a channel disconnect user interface selectable by a user; and
   (f) a processor connected to the switching devices and adapted to provide the switching device control signal to control the switching devices in each channel selected using the channel disconnect selection user interface to prevent a signal from being applied to the signal amplifiers from the electrodes only in such selected channels when the channel disconnect user interface is selected and to provide the switching device control signal to control the switching devices in the selected channels to allow application of a signal to the amplifiers in such selected channels from the corresponding electrodes when the channel disconnect user interface is deselected.

9. The medical signal monitoring system of claim 8 wherein the plurality of switching devices are selected from the group of switching devices consisting of transistors and relays.

10. The medical signal monitoring system of claim 8 wherein at least one of the electrodes is connected by a lead to an input of a corresponding one of the signal amplifiers via a corresponding one of the switching devices.

11. The medical signal monitoring system of claim 8 comprising additionally a display and a user input device connected to the processor and wherein the channel disconnect selection user interface and the channel disconnect user interface are graphical user interfaces generated by the processor, displayed on the display, and selectable using the user input device.

12. The medical signal monitoring system of claim 11 wherein the channel disconnect selection user interface and the channel disconnect user interface include check boxes which are selectable using the user input device.

13. A signal monitoring method, comprising the steps of:
   (a) providing a plurality of signals to be monitored on channels to a plurality of corresponding signal amplifiers;
   (b) selecting selected ones of the plurality of signal channels using a channel disconnect selection user interface;
   (c) selecting a channel disconnect user interface;
   (d) disconnecting selected signals to be monitored from the corresponding signal amplifiers only in the signal channels selected using the channel disconnect selection user interface in response to the selection of the channel disconnect user interface;
   (e) deselecting the channel disconnect user interface; and
   (f) reconnecting the selected signals to be monitored to the corresponding signal amplifiers in the signal channels selected using the channel disconnect selection user interface in response to the deselection of the channel disconnect user interface.

14. The method of claim 13 wherein the step of disconnecting selected signals to be monitored from the corresponding signal amplifiers includes the step of opening switching devices connected to inputs of the signal amplifiers in the signal channels selected using the channel disconnect selection user interface, and wherein the step of reconnecting the selected signals to be monitored to the corresponding signal amplifiers includes the step of closing switching devices connected to inputs of the signal amplifiers in the signal channels selected using the channel disconnect selection user interface.

15. The method of claim 14 wherein the steps of opening and closing selected switching devices includes the steps of applying control signals to transistor switching devices.

16. The method of claim 13 wherein the step of providing a plurality of signals to be monitored includes the step of attaching a plurality of electrodes to a subject to detect a plurality of electrophysiologic signals to be monitored.

17. The method of claim 16 comprising additionally the step of providing electrical stimulation to the subject, and wherein the step of selecting the channel disconnect user interface is performed before providing electrical stimulation to the subject and the step of deselecting the channel disconnect user interface is performed after providing the electrical stimulation to the subject.

18. The method of claim 13 wherein the steps of selecting selected ones of the plurality of signal channels and selecting the channel disconnect user interface includes the steps of generating channel disconnect selection and channel disconnect graphical user interfaces, displaying the channel disconnect selection and channel disconnect graphical user interfaces on a display, and selecting the channel disconnect selection and channel disconnect graphical user interfaces using a user input device.

19. The method of claim 17 wherein the steps of generating the channel disconnect selection graphical user interface and the channel disconnect graphical user interface includes the steps of generating and displaying the channel disconnect selection and channel disconnect graphical user interfaces as check boxes.

20. A medical signal monitoring system, comprising:
(a) a plurality of electrodes adapted to be positioned on a subject to detect electrophysiologic signals;
(b) a plurality of signal amplifiers coupled to the plurality of electrodes such that each electrode and a corresponding signal amplifier form a signal channel, wherein the signal amplifiers are adapted to amplify electrophysiologic signals;
(c) a switching device connected between the electrode and the signal amplifier in each signal channel, each switching device being responsive to a switching device control signal to control the switching device to prevent a signal from being applied to a signal amplifier from a corresponding electrode, or to allow application of a signal to the signal amplifier from the corresponding electrode;
(d) a channel disconnect selection user interface to allow a user to indicate selected ones of the signal channels;
(e) a processor adapted to control the providing of an electrical stimulation signal to the subject, connected to the switching devices, and adapted to provide automatically the switching device control signal to control the switching devices in each channel selected using the channel disconnect selection user interface to prevent a signal from being applied to the signal amplifiers from the electrodes only in such selected channels during the providing of an electrical stimulation signal to the subject, and to provide automatically the switching device control signal to control the switching devices in the selected channels to allow application of a signal to the amplifiers in such selected channels from the corresponding electrodes after the providing of an electrical stimulation signal to the subject is complete.

21. The medical signal monitoring system of claim 20 wherein the plurality of switching devices are selected from the group of switching devices consisting of electrodes and relays.

22. The medical signal monitoring system of claim 20 wherein at least one of the electrodes is connected by a lead to an input of a corresponding one of the signal amplifiers via a corresponding one of the switching devices.

23. The medical signal monitoring system of claim 20 comprising additionally a display and a user input device connected to the processor and wherein the channel disconnect selection user interface is a graphical user interface generated by the processor, displayed on the display, and selectable using the user input device.

24. The medical signal monitoring system of claim 23 wherein the channel disconnect selection user interface includes a check box which is selectable using the user input device.

25. A signal monitoring method, comprising the steps of:
(a) providing a plurality of electrophysiologic signals from a subject on signal channels to a plurality of corresponding signal amplifiers;
(b) selecting selected ones of the plurality of signal channels using a channel disconnect selection user interface;
(c) providing an electrical stimulation signal to the subject;
(d) automatically disconnecting signals from the corresponding signal amplifiers only in the signal channels selected using the channel disconnect selection user interface a first time period prior to the providing of the electrical stimulation signal to the subject;
(e) automatically reconnecting the selected signals to be monitored to the corresponding signal amplifiers in the signal channels selected using the channel disconnect selection user interface a second time period following the providing of the electrical stimulation signal to the subject.

26. The method of claim 25 comprising additionally the step of selecting durations of the first and second time periods.

27. The method of claim 25 wherein the step of disconnecting signals from the corresponding signal amplifiers includes the step of opening switching devices connected to inputs of the signal amplifiers in the signal channels selected using the channel disconnect selection user interface, and wherein the step of reconnecting the signals to the corresponding signal amplifiers includes the step of closing switching devices connected to inputs of the signal amplifiers in the signal channels selected using the channel disconnect selection user interface.

28. The method of claim 25 wherein the steps of opening and closing the switching devices includes the steps of applying control signals to the switching devices.

29. The method of claim 25 wherein the step of providing a plurality of electrophysiologic signals includes the step of attaching a plurality of electrodes to the subject.

30. The method of claim 25 wherein the step of selecting selected ones of the plurality of signal channels includes the steps of generating a channel disconnect selection graphical user interface, displaying the channel disconnect selection graphical user interface on a display, and selecting the channel disconnect selection graphical user interface using a user input device.

31. The method of claim 30 wherein the step of generating the channel disconnect selection graphical user interface includes the steps of generating and displaying the channel disconnect selection graphical user interface as a check box.

* * * * *